United States Patent
Bailly et al.

(10) Patent No.: US 7,833,234 B2
(45) Date of Patent: Nov. 16, 2010

(54) APPLIANCE FOR STORING, DISTRIBUTING AND PLACING SURGICAL FASTENERS

(75) Inventors: Pierre Bailly, Caluire (FR); Michel Therin, Lyons (FR)

(73) Assignee: Sofradim Production, Trevoux (FR)

( * ) Notice: Subject to any disclaimer, the term of this patent is extended or adjusted under 35 U.S.C. 154(b) by 108 days.

(21) Appl. No.: 11/239,150

(22) Filed: Sep. 30, 2005

(65) Prior Publication Data

US 2006/0122636 A1 Jun. 8, 2006

(30) Foreign Application Priority Data

Oct. 6, 2004 (FR) ................... 04 10585

(51) Int. Cl.
*A61B 17/10* (2006.01)

(52) U.S. Cl. .................................... 606/143

(58) Field of Classification Search ........... 606/142, 606/143, 139, 140; 227/176, 176.1, 19, 67, 227/68, 77, 175.1, 901; 604/62, 57, 60, 136, 604/137, 139

See application file for complete search history.

(56) References Cited

U.S. PATENT DOCUMENTS

| | | | |
|---|---|---|---|
| 4,006,747 A * | 2/1977 | Kronenthal et al. ......... 606/144 |
| 5,376,097 A | 12/1994 | Phillips | |
| 5,470,337 A | 11/1995 | Moss | |
| 5,544,802 A * | 8/1996 | Crainich ................. 227/176.1 |
| 5,601,571 A | 2/1997 | Moss et al. | |
| 5,690,675 A * | 11/1997 | Sawyer et al. ............... 606/229 |
| 5,810,848 A * | 9/1998 | Hayhurst ..................... 606/144 |
| 5,997,552 A * | 12/1999 | Person et al. ................ 606/139 |
| 6,152,935 A * | 11/2000 | Kammerer et al. .......... 606/144 |
| 6,520,972 B2 * | 2/2003 | Peters ......................... 606/143 |
| 6,551,333 B2 * | 4/2003 | Kuhns et al. ................ 606/151 |
| 6,592,596 B1 * | 7/2003 | Geitz ......................... 606/139 |
| 6,779,701 B2 * | 8/2004 | Bailly et al. ............. 227/176.1 |
| 7,066,944 B2 * | 6/2006 | Laufer et al. ................ 606/151 |
| 7,087,064 B1 * | 8/2006 | Hyde .......................... 606/142 |
| 7,632,287 B2 * | 12/2009 | Baker et al. ................. 606/151 |
| 2002/0087170 A1 | 7/2002 | Kuhns et al. | |
| 2003/0097148 A1 | 5/2003 | Valimaa et al. | |

FOREIGN PATENT DOCUMENTS

| FR | 2 308 349 A | 11/1979 |
|---|---|---|
| WO | WO 00/49950 A1 | 8/2000 |
| WO | WO 03/043503 | 5/2003 |
| WO | WO 03/075773 A1 | 9/2003 |

\* cited by examiner

*Primary Examiner*—Todd E Manahan
*Assistant Examiner*—Lindsey Bachman
(74) *Attorney, Agent, or Firm*—Carter, DeLuca, Farrell & Schmidt, LLP

(57) ABSTRACT

An appliance for storing, distributing and placing surgical fasteners comprises a handgrip body and an elongate element attached to the handgrip. The elongate element includes a magazine slide adapted to be displaced in the elongate element by a control rod. The control rod can be, in turn, actuated by the handgrip. The magazine slide also has surgical fasteners. Each surgical fastener has an anchoring bar, a catching bar and a connecting strip. A distal part of the anchoring bar has a conical shape. A distal end of the distal part of the anchoring bar has a hemispherical shape.

12 Claims, 8 Drawing Sheets

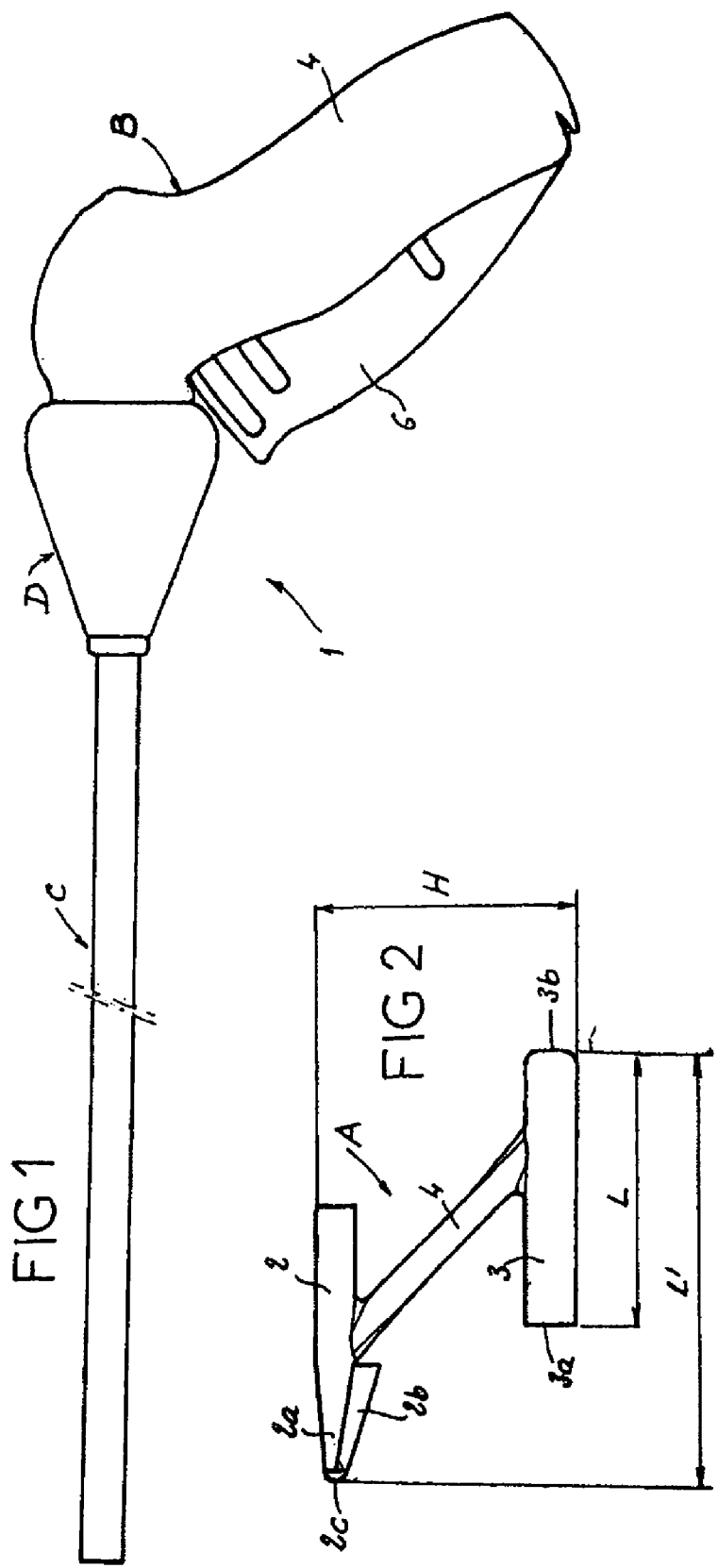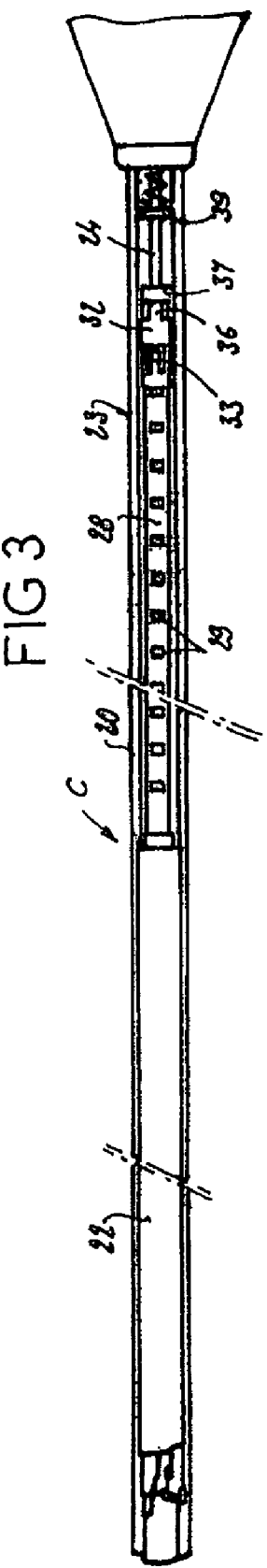

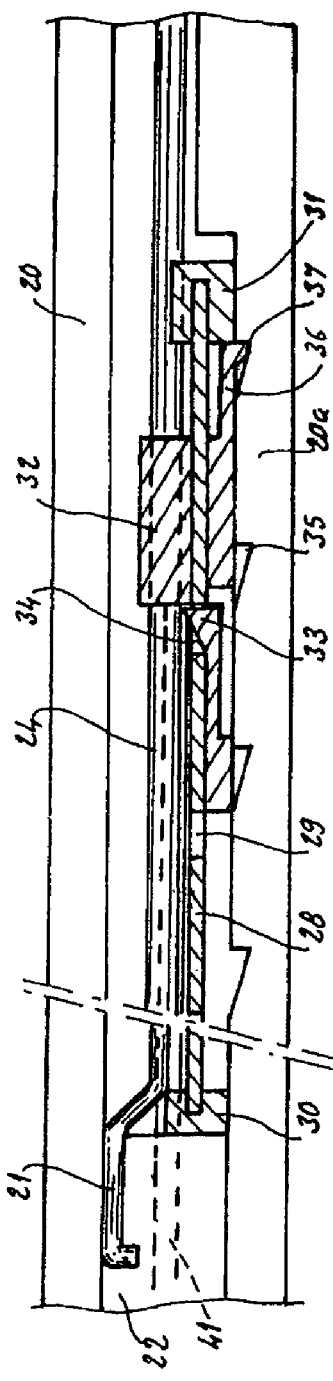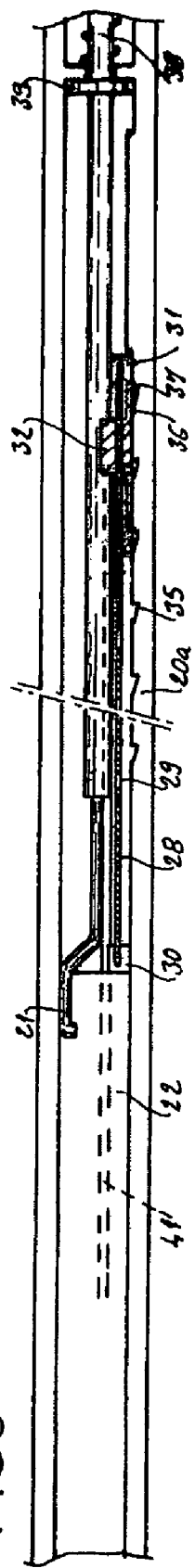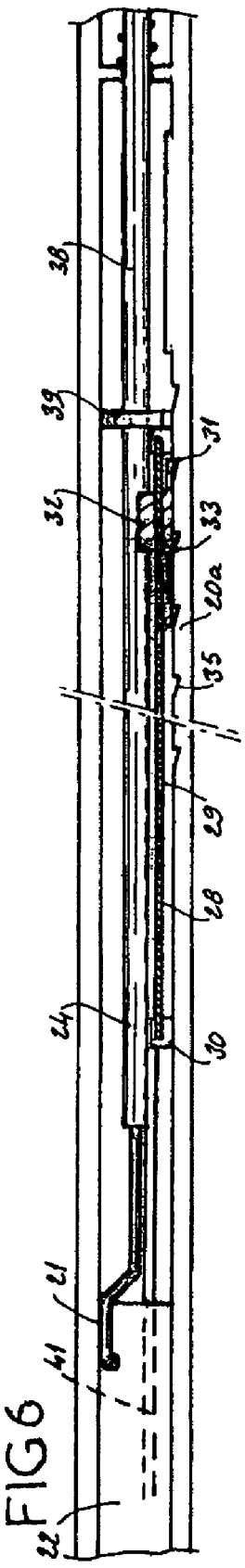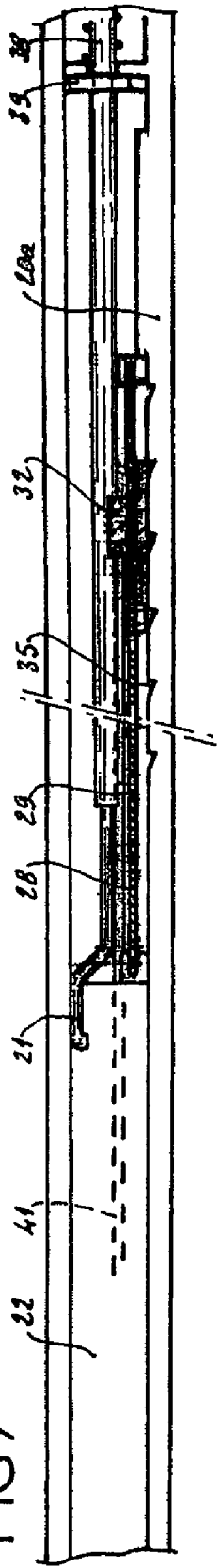

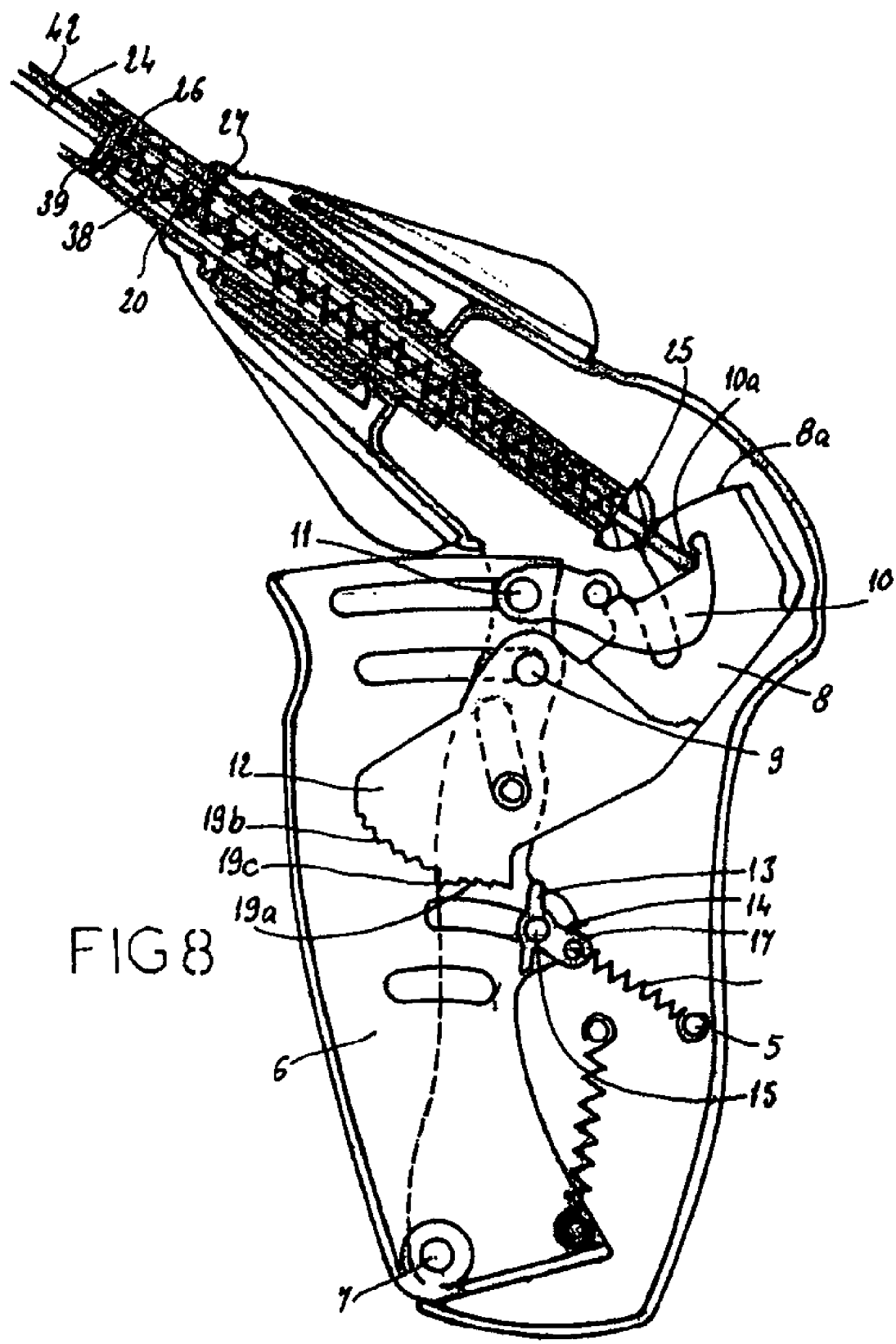

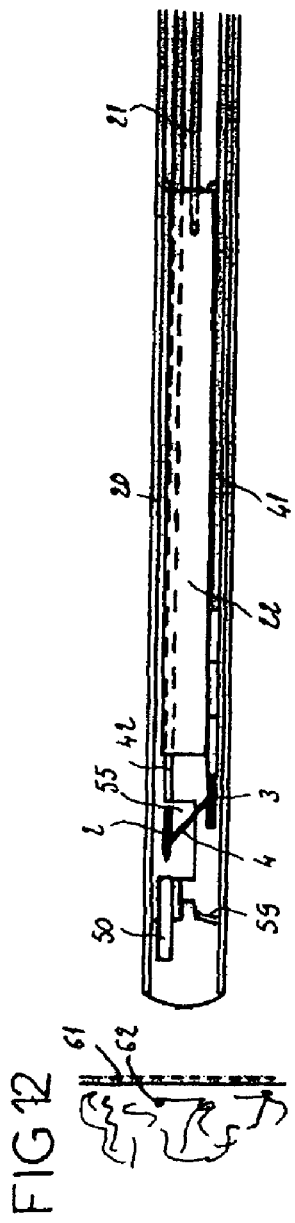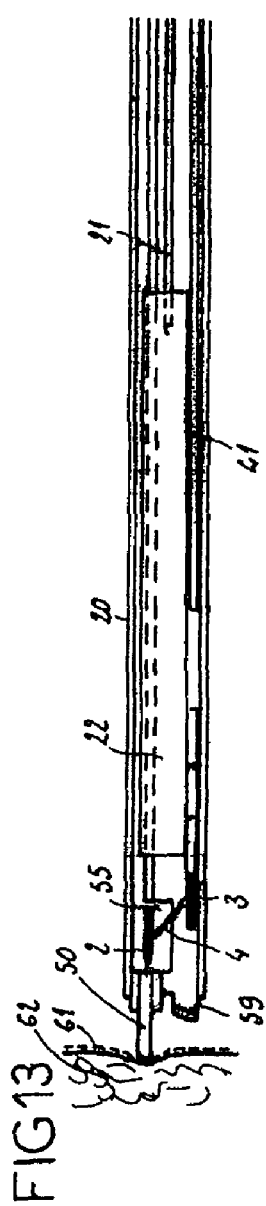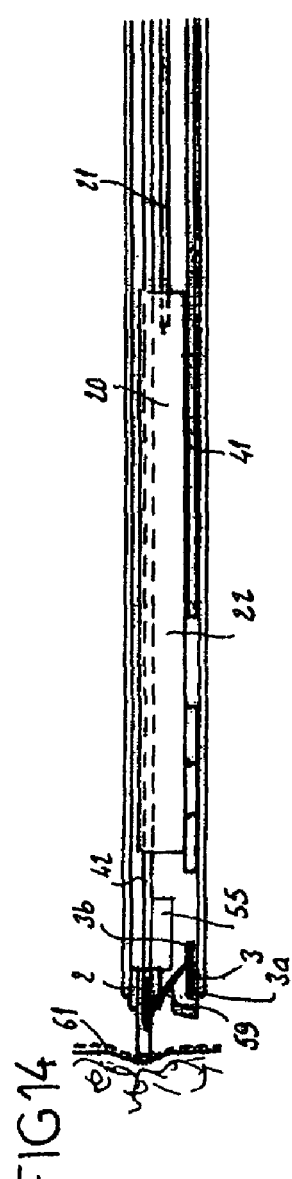

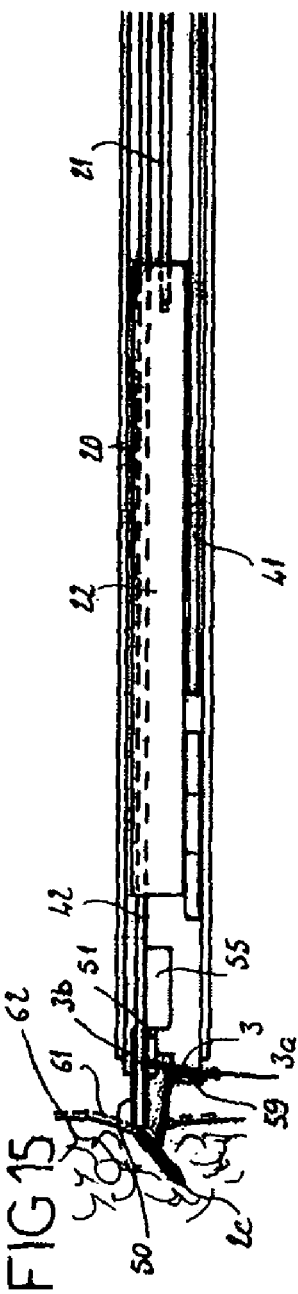
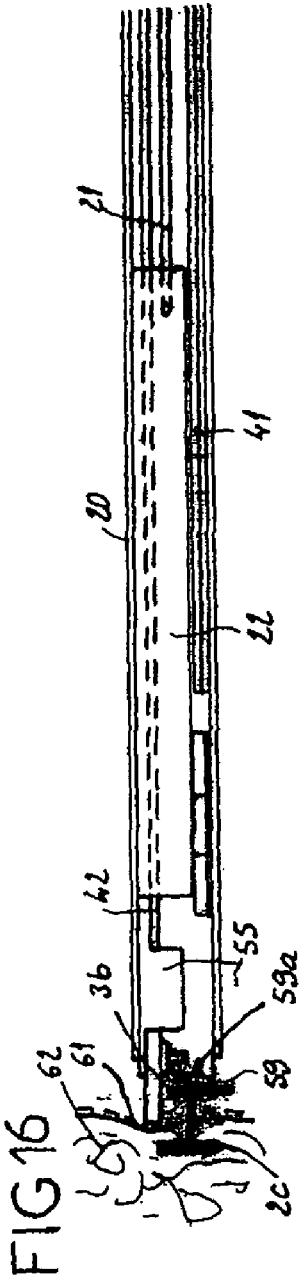
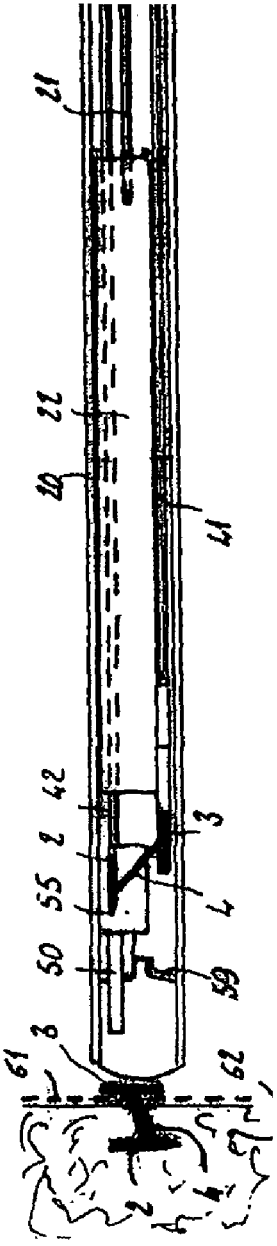
FIG 15
FIG 16
FIG 17

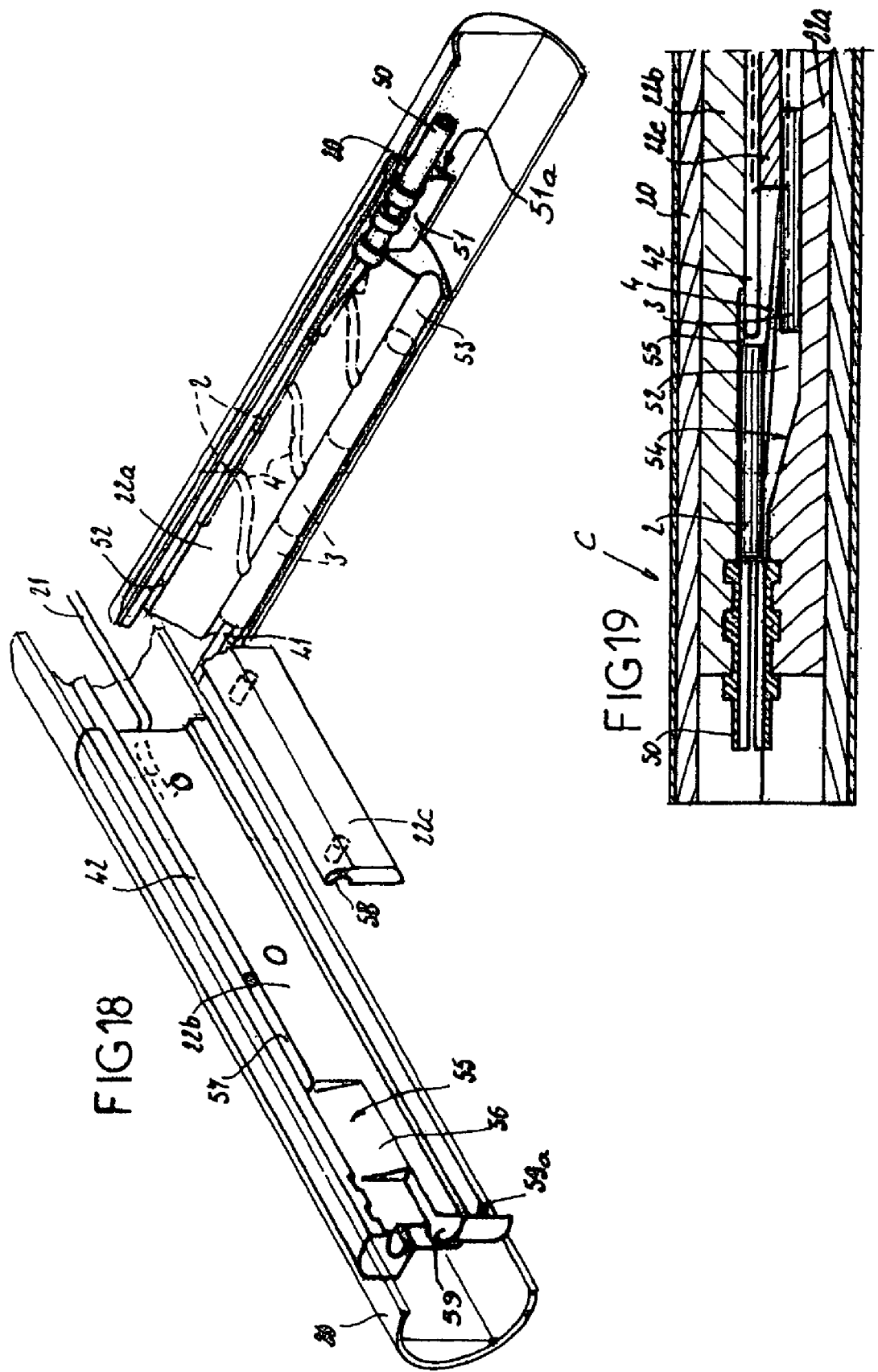

APPLIANCE FOR STORING, DISTRIBUTING AND PLACING SURGICAL FASTENERS

CROSS-REFERENCE TO RELATED APPLICATIONS

This application is related and claims priority to French Patent Application No. 04.10585, filed on Oct. 6, 2004, which is hereby incorporated by reference.

BACKGROUND

1. Technical Field

The present invention relates to an appliance for distributing and placing a couched I-shaped surgical fastener, for example for fixing parietal and visceral reinforcements, said appliance and said fastener permitting a placement that does not cause trauma to the tissues.

2. Background of Related Art

An appliance for distributing and placing I-shaped surgical fasteners is already known from WO03/075773. The fasteners described in said document comprise an anchoring bar, a catching bar and a connecting strip. They are introduced into the tissues to be fixed by means of a slotted hollow needle with a sharp bevelled end which passes through said tissues in order to deliver the fastener to the site where it is to assume its function. Thus, in this document, the needle passes through the flesh and, because of its hollow shape, may cause bleeding, and also a phenomenon known as "coring". "Coring" is understood as the removal of a quantity of flesh corresponding to the internal volume of that part of the hollow needle having penetrated the flesh. Thus, the appliance described in said document poses risks of haemorrhage.

Moreover, in WO03/075773, when the needle with its bevelled point pricks the fabric of the prosthesis at a thread crossover or in the area of a thread, it passes through said thread or threads, possibly separating the filaments composing these threads, and this may produce resistance and packing. This damages the threads and, consequently, the prosthesis. The resistance produced may also block the mechanism of the appliance and render it unusable.

Another problem encountered with the appliance described in WO03/075773 is that, because of the necessary penetration of the bevelled needle into the flesh, the appliance does not allow a prosthesis to be stapled in the area of an anatomical structure of small thickness, that is to say in particular a thickness less than the length of the needle part passing through the flesh.

The present invention aims to remedy these problems by proposing an appliance for distributing a particular couched I-shaped fastener and able to deliver said fastener in a manner that does not cause trauma to the flesh and without causing any coring phenomenon, thereby limiting the risks of bleeding.

SUMMARY

The present invention relates to an appliance for storing, distributing and placing couched I-shaped surgical fasteners (A), comprising a handgrip body (B) equipped with at least one control means, and an elongate element (C) attached and fixed to the handgrip, in which appliance the elongate element (C) is made up of a body of tubular overall shape containing:
near its distal end, a magazine slide itself containing couched I-shaped fasteners having an anchoring bar, a catching bar and a connecting strip, said magazine slide being displaceable in the elongate element by a control rod which can be actuated by the control means of the handgrip and, on the other hand, secured to a slotted and longitudinal hollow ejection barrel projecting from the distal end of said magazine slide and able to project from the elongate element (C),
and, in its tubular body, on the one hand, means for distributing the stored fasteners (A) one by one, this distribution involving the transfer of the anchoring bar of the first fastener into a receiving seat arranged in the continuation of the ejection barrel and, on the other hand, an ejection plunger which can be displaced by the control means of the handgrip and which is arranged in alignment with the ejection barrel so as to push the anchoring bar of the first fastener into the latter, characterized in that:
the distal part of the anchoring bar of the fasteners (A) is of conical shape, and the distal end of this distal part is of hemispherical shape,
the surface of the distal end of the ejection barrel is arranged in a plane substantially perpendicular to the longitudinal axis of the tubular body.

The present invention also relates to a couched I-shaped surgical fastener comprising an anchoring bar, a catching bar and a connecting strip, characterized in that the distal part of the anchoring bar of the fastener is of conical shape, and the distal end of this distal part is of hemispherical shape.

The present application also relates to an assembly comprising at least one couched I-shaped surgical fastener (A) and an appliance for storing, distributing and placing such fasteners (A), comprising a handgrip body (B) equipped with at least one control means, and an elongate element (C) attached and fixed to the handgrip, in which appliance the elongate element (C) is made up of a body of tubular overall shape containing:
near its distal end, a magazine slide itself containing couched I-shaped fasteners (A) having an anchoring bar, a catching bar and a connecting strip, said magazine slide being displaceable in the elongate element by a control rod which can be actuated by the control means of the handgrip and, on the other hand, secured to a slotted and longitudinal hollow ejection barrel projecting from the distal end of said magazine slide and able to project from the elongate element (C),
and, in its tubular body, on the one hand, means for distributing the stored fasteners (A) one by one, this distribution involving the transfer of the anchoring bar of the first fastener into a receiving seat arranged in the continuation of the ejection barrel and, on the other hand, an ejection plunger which can be displaced by the control means of the handgrip and which is arranged in alignment with the ejection barrel so as to push the anchoring bar of the first fastener into the latter, characterized in that:
the distal part of the anchoring bar of the fasteners (A) is of conical shape, and the distal end of this distal part is of hemispherical shape,
the surface of the distal end of the ejection barrel is arranged in a plane substantially perpendicular to the longitudinal axis of the tubular body.

In the present application, distal end of a component is understood as the end farthest from the person using the appliance, and proximal end is understood as the end nearest to the person using the appliance.

Placement of a fastener using the appliance according to the invention does not cause trauma to the flesh. This is because the ejection barrel of the appliance according to the invention has a flat distal end which does not incise the flesh or the prosthesis, nor does it penetrate them.

Thus, in one embodiment of the invention, the ejection barrel can be made of metal and fixed on the magazine slide.

In a preferred embodiment of the invention, the ejection barrel is made of plastic and is moulded in one piece with the magazine slide. The surface of the distal end of the ejection barrel is preferably blunt. Such a configuration is preferred because such an ejection barrel is especially non-traumatizing in respect of the flesh. Such an ejection barrel does not therefore cause the phenomenon of coring. It therefore does not cause removal of a quantity of flesh capable of causing haemorrhage.

Moreover, the specific shape of the fastener according to the invention, as a conical portion ending in a hemisphere, and the specific nature of said fastener allow the latter to first force a passage through the meshes of the prosthesis without damaging the threads thereof, and therefore without destroying this prosthesis, thereafter through the human tissues without causing bleeding. The risks of packing and of haemorrhage are also avoided.

In a preferred embodiment of the invention, the fastener A is made of biocompatible plastic. It is preferably made of bioabsorbable plastic. Even more preferably, the bioabsorbable plastic is a lactic acid polymer.

By virtue of its plastic nature, the fastener slides and spreads apart the threads of the prosthesis without damaging them, so as to establish a passage at the centre of the mesh of the prosthesis.

Finally, it is possible, by virtue of the assembly according to the invention, to staple a prosthesis in the area of an anatomical structure of small thickness, for example in the area of Cooper's ligament, the thickness of which may be less than 3 mm, and to do so without the proximity of a solid structure, such as the os pubis, creating an obstacle. This is because, in the case where the fastener according to the invention comes into contact with the os pubis, its hemispherical end allows it to slide gently on this bone and to pivot easily in the tissues so as to take up position and perform its role of effective fixation.

Indeed, with the appliance according to the invention, the fact that the ejection barrel does not penetrate the prosthesis or the human tissues means that the fastener has more room in the human tissue to effect the rotation of the anchoring bar during positioning of the fastener at the moment of its ejection, compared to the case of an appliance of the prior art in which a bevelled needle also penetrates into the tissues. In particular, according to the present invention, since the ejection barrel does not have a bevelled end, the fastener can escape more quickly from the ejection barrel.

In a preferred embodiment of the invention, the length of the projecting part of the ejection barrel at the moment of ejection is less than or equal to 3 mm.

In a preferred embodiment of the invention, the total length L' of the fastener (A) in its operating position is less than or equal to 10.5 mm.

In a preferred embodiment of the invention, the total height H of the fastener (A) in its operating position is less than or equal to 6.1 mm.

In particular, according to the invention, the overall size of the fastener is minimal. It is thus possible to store, for example, up to twenty fasteners within the magazine slide.

In a preferred embodiment of the invention, the handgrip is provided with a double non-return system ensuring appropriate use of the appliance and avoiding its becoming jammed.

In a preferred embodiment of the invention, the elongate element C comprises a step-by-step system able to move the stored fasteners A by a step P having a value equal to the length L of the catching bar of a fastener A, this step-by-step system comprising a rack effecting a drawer movement upon each ejection and being equipped with a shuttle which is mounted so as to slide on this rack, this shuttle cooperating with fixed notches of the magazine slide in order to advance by a step P on the rack upon each ejection.

Other characteristics and advantages will become evident from the description which follows with reference to the appended schematic drawing which depicts one embodiment of the assembly according to the invention.

BRIEF DESCRIPTION OF THE DRAWINGS

FIG. 1 is a side view of an appliance according to the invention, at rest,

FIG. 2 is a side view of a fastener according to the invention,

FIG. 3 is a sectional view of the elongate element,

FIG. 4 is a partial cross section showing the step-by-step system and the shuttle, FIGS. 5 to 7 are partial cross sections showing the functioning of the step-by-step system.

FIG. 8 is a sectional view of the handgrip in the rest position,

FIGS. 12 to 17 show the different phases in the ejection of a fastener using the appliance according to the invention, FIG. 18 is an exploded and enlarged perspective view of the front end of the elongate element and of the magazine slide, FIG. 19 is a sectional view of the front end of the elongate element.

DETAILED DESCRIPTION OF THE EMBODIMENTS

Figure 9:
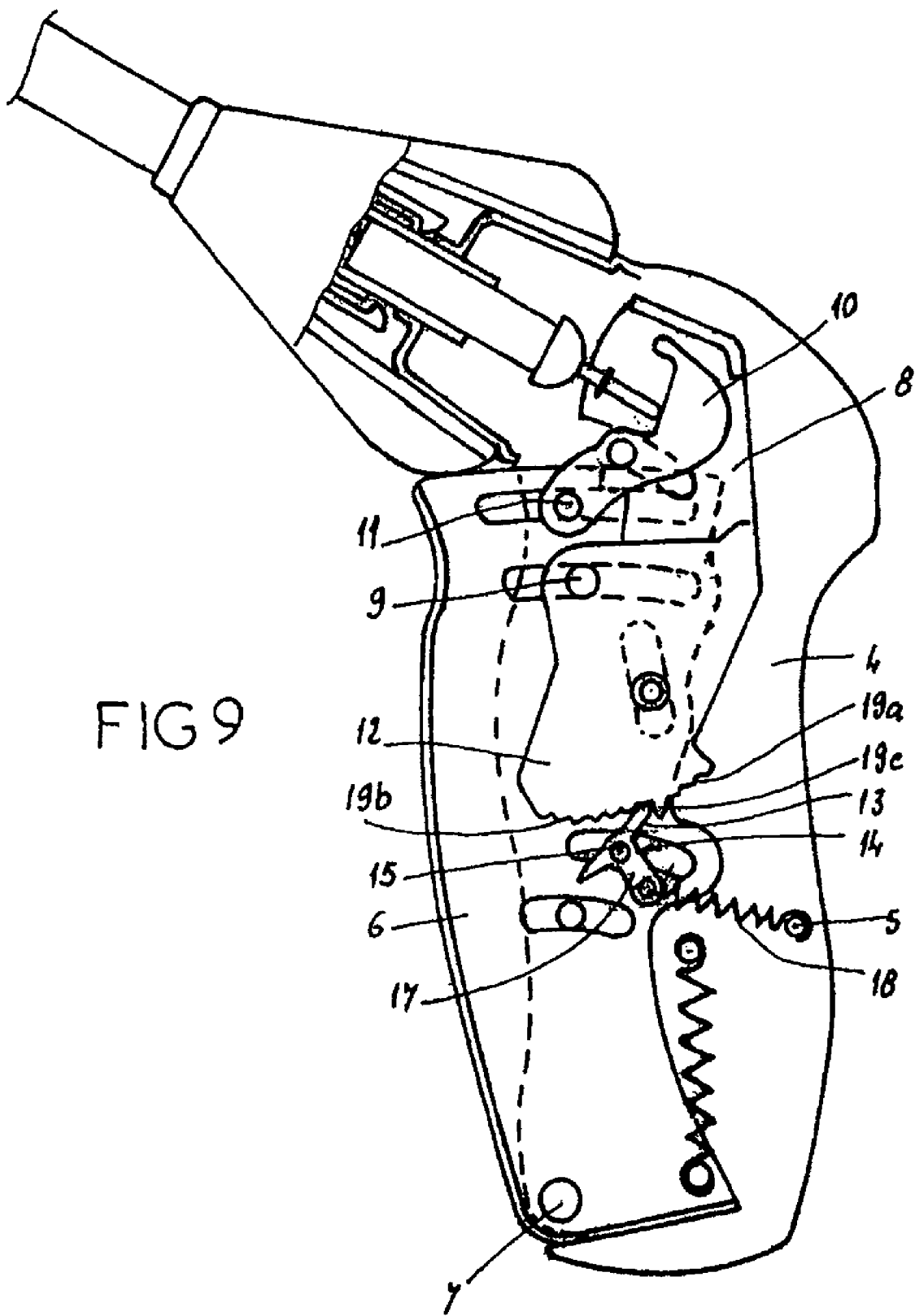
FIGS. 9 to 11 show the functioning of the double non-return system of the handgrip.

The appliance 1 shown in FIG. 1 is intended to distribute staples A which, as shown in FIG. 2, have the overall shape of a couched I made up of two parallel bars, namely an anchoring bar 2 and a catching bar 3, which are connected by an inclined connecting strip 4. The distal part 2a of the anchoring bar 2 has a conical shape. This distal part 2a can comprise a projecting notch 2b for protecting the anchoring bar/connecting strip junction which is stressed at the moment of ejection and placement of the staple. The distal end 2c of the anchoring bar 2 is of hemispherical shape. The distal part of the anchoring bar 2 is engaged first in the prosthesis and in the human body. Its particular shape described above permits easy engagement of the fastener through the prosthesis and the human tissues. The hemispherical part, combined with the conical part, allows the fastener to establish a passage through the meshes of the prosthesis by sliding along the threads and spreading them apart without damaging them. Thus, the distal part of the anchoring bar 2 passes through a mesh of the prosthesis without producing resistance or packing, and it then penetrates easily into the human tissues by virtue of its conical and tapered shape, but without causing trauma of said tissues, on account of the hemispherical and thus gentle and blunted shape of its distal end.

The fastener A is made of plastic, especially of biocompatible plastic, and preferably bioabsorbable plastic.

The connecting strip 4 is connected approximately to the centre of the anchoring bar 2. The catching bar 3 comprises a distal part 3a and a proximal part 3b. The connecting strip 4 is connected to the catching bar 3 at a point close to the centre of this catching bar 3, slightly offset towards its proximal part 3b. The connecting strip is inclined by approximately 45° relative to the anchoring bar and catching bar. This particular embodiment of the fastener makes it possible to reduce the overall size of the fastener while giving it sufficient strength to ensure effective fixation of the prosthesis in the tissues; it is thus also possible to use this fastener to staple anatomical structures of small thickness and to store a large number of fasteners inside the appliance 1, as will be seen below. The total length L' of the fastener (A), in its operating position as shown in FIG. 2, namely from the distal end 2c of its anchoring bar 2 to the proximal end 3b of its catching bar 3, is preferably less than or equal to 10.5 mm. The height H of the fastener (A), in its operating position as shown in FIG. 2, is preferably less than or equal to 6.1 mm.

As is shown in FIG. 1, the appliance 1 is made up of two elements, namely a grip assembly B and an elongate element C which are connected to one another with the aid of a bushing D. As the ejection barrel 50 (see FIG. 18) is eccentric, the bushing D makes it possible to pivot the elongate element C and to keep it fixed in rotation in the position preferred by the surgeon for projection of the ejection barrel 50.

As is shown in FIG. 8, the grip element B comprises a handgrip body 4 formed in two symmetrical parts which are joined by ultrasonic welding or by rivets or screws 5, a handgrip 6 articulated on a transverse axle 7 of the body, a first control lever 8 articulated on a transverse axle 9 of the body and having a cam profile 8a, and a second control lever 10 articulated on a transverse axle 11 of the body and having a cam profile 10a.

The lower part of the first control lever 8 forms an arc of a circle 12 provided with teeth which are intended to cooperate with the branch 13 of a knurled wheel 14 articulated on a transverse axle 15 of the body throughout the surgical procedure, namely a phase of positioning of the appliance during which the surgeon is able to cause the ejection barrel 50 (see FIG. 18) to emerge without proceeding with the ejection itself, then an ejection phase, and finally a phase in which the appliance is returned to its rest state, as will be explained hereinbelow. The knurled wheel 14 comprises a second, retaining branch 17 connected to a spring 18 whose fixed end is attached to the handgrip body 4. The arc of a circle 12 comprises a first series of teeth 19a of slight inclination and a second series of teeth 19b of strong inclination, the two series of teeth being separated by a tooth 19c of larger size.

As is shown in FIG. 3, the elongate element C comprises a tubular body 20 in which a magazine slide 22 is slidably mounted. The body 20 also comprises a step-by-step system 23 whose operation will be explained in more detail with reference to FIGS. 4 to 7.

As is shown in FIG. 4, the magazine slide 22 is connected to a control rod 24 with the aid of an axial rod 21 of smaller diameter which is bent at right angles. As is shown in FIG. 8, the control rod 24 bears on the cam profile 10a of the second control lever 10. The tubular body 20 is itself made up of two semicylindrical plastic shells assembled along their diametral plane by welding, interlocking or bonding, each of the shells itself being monolithic. The body 20 is preferably arranged in a tubular metal band (not shown) serving to strengthen the elongate element C.

As is shown in FIG. 8, the tubular body 20 also comprises a piston 25 penetrating into the handgrip body 4 and held on the cam profile 8a of the first control lever 8 by means of a spring 27 which bears on a flange 26 of the tubular body 20. The piston 25 is integral with a tube 38 which extends through it and which also extends through the spring 27. The distal end of this tube 38 is equipped with a flange 39 on which is fixed a push rod 42 extending in the magazine slide.

The step-by-step system 23 is described in FIG. 3 and in FIG. 4 which is a sectional view through a plane offset by 90° with respect to the sectional plane of FIG. 3. It comprises a rack 28, for example of metal, equipped with notches 29 spaced apart regularly with a step P having a value equal to the length L (FIG. 2) of the catching bar 3 of a fastener A. The rack 28 is equipped, at its ends, with a distal block 30 and a proximal block 31, preferably made of plastic. A shuttle 32, preferably made of plastic, is mounted so as to slide on the rack 28. This shuttle 32 comprises a distal tab 33 with an inclined face 34 permitting relative displacement, in the proximal direction, of the rack 28 with respect to the shuttle 32. This same tab 33 snaps into the notches 29 of the rack 28 to prevent relative displacement, in the distal direction, of the rack 28 with respect to the shuttle 32, as is shown in FIG. 4.

The step-by-step system 23 also comprises a series of notches 35 which are formed on the inner face of one shell 20a of the tubular body 20 opposite the rack 28 and are spaced apart regularly by a step P having a value equal to the length L (FIG. 2) of the catching bar 3 of a fastener A. The shuttle 32 comprises a proximal tab 36 with a projection 37 permitting relative displacement, in the distal direction, of the shuttle and rack with respect to the shell 20a. This projection 37 snaps into the notches 35 of the shell 20a in order to prevent return of the shuttle 32 in the proximal direction.

Mounted on the shuttle 32 there is an abutment rod 41 which extends longitudinally and which penetrates into the magazine slide 22 in the groove 53 (see FIG. 18) serving as seats for the catching bars 3 of the fasteners A.

As is shown in FIG. 18, the magazine slide is formed by two plastic shells 22a and 22b which are assembled, by bonding or welding, along their longitudinal and vertical mid-plane, enclosing an insert plate 22c.

At its distal end, the shell 22a is fixed to an ejection barrel 50. This ejection barrel 50 is hollow and slotted, and the surface of its distal end is arranged in a plane substantially perpendicular to the longitudinal axis of the tubular body 20. As used herein, the term "substantially perpendicular . . . " means that the distal end of the ejection barrel is substantially flat such that the barrel is shaped and configured not to incise, penetrate, core or effect removal of tissue. This ejection barrel 50 is intended to receive the anchoring bar 2 of a fastener A. This ejection barrel 50 is made of plastic and is moulded in one piece with the magazine slide 22.

Near its edges, the shell 22a comprises two longitudinal grooves, namely a groove 52 serving as seats for the anchoring bars 2 of the fasteners A, and a groove 53 serving as seats for the catching bars 3 of the same fasteners. These two grooves are in one and the same vertical plane, distinct from the one passing through the ejection barrel 50. The groove 53 serving as seats for the catching bars 3 opens freely from the front end of the shell 22a, while the groove 52 serving as seats for the anchoring bars 2 dies out against an inclined plane visible in FIG. 19. The latter encourages the anchoring bar 2 of the first fastener to move transversely until this bar comes behind and into the longitudinal axis of the ejection barrel, in a receiving seat 55 as shown in FIG. 18.

The shell 22a further comprises, beside the ejection barrel 50, a rib 51 which projects downwards and which, above the path of a catching bar leaving the groove 53 serving as seats for the catching bars 3, has a sloping face 51a.

FIG. 19, which depicts the appliance in the rest position, shows that, in this position, the push rod 42 is set back from the rear end of the ejection barrel 50 to uncover the receiving seat 55 formed in the other shell 22b.

FIG. 18 shows that the receiving seat 55 for the anchoring bar 2 of the first fastener is extended downwards by an inclined face 56 that supports the connecting strip 4 of the fastener. This shell 22b also has a semicylindrical groove 57 which, together with a complementary groove 58 formed in the plate 22c, forms a channel for guiding the push rod 42. This channel is coaxial with the ejection barrel 50. The proximal end of the shell 22b is connected to the axial rod 21, itself connected to the control rod 24. In its part lying below the ejection barrel 50, the distal end of the shell 22b is equipped with a transverse finger 59 projecting towards the other shell, having a sloping face 59a and the benefit of which will be specified later on.

The insert plate 22c has a width allowing it to be inserted between the grooves 52 and 53 of the shell 22a and a thickness allowing it to form, with this shell 22a, a corridor leaving a passage for the connecting strips 4 of the fasteners A.

The magazine slide 22 thus formed has a length which allows it, for example, to store twenty fasteners A.

When the appliance is at rest, the handgrip 6 is in the position depicted in FIG. 8, with the control rod 24 bearing on the cam profile 10a of the second control lever 10, and the piston 25 bearing on the cam profile 8a of the first control lever. The magazine slide 22 is in a retracted position inside the tubular body 20. The ejection barrel 50 is retracted inside the body, and the push rod 42 which uncovers the receiving seat 55 exerts no force on the anchoring bar 2 arranged in this seat. Likewise, the catching bars 3 of the fasteners A on standby in the magazine are in contact with one another, while the catching bar of the last fastener is near, with or without contact, the end of the abutment rod 41.

In use, for example by a laparoscopic approach, the elongate element C of the appliance is introduced, with the ejection barrel 50 retracted, into a trocar. Engagement is performed until there is proximity to or contact with the prosthesis 61 that is to be stapled to the human tissues 62, as is shown in FIG. 12. The surgeon then has the possibility of deploying the ejection barrel 50 without in so doing triggering the ejection of the fastener A, as shown in FIG. 13. To do this, the surgeon presses the handgrip 6. In a first part of the travel, the second control lever 10 pivots about its axis 11. The cam profile 10a bears on the rod 24 which is displaced in the distal direction and pushes the magazine slide 22 also in the distal direction, causing the ejection barrel 50 to project out of the tubular body 20.

Also during this first part of its travel, the branch 13 of the knurled wheel 14 cooperates with the series of teeth 19a of the arc of a circle 12 of the first control lever 8. Provided the branch 13 has not passed the tooth of larger size 19c, the surgeon can relax his force on the handgrip and return to the rest position. The reason is that, because the end of the branch 13 is rounded, it does not definitively mesh in the slight inclines of the teeth 19a, and these therefore allow the branch 13 to return to its initial position. Thus, as long as he is not exerting a force sufficient to pass the tooth 19a, the surgeon can cause the ejection barrel 50 to project and can then return it again into the tubular body 20 without triggering ejection of the fastener A. This allows him to test various positions of the appliance before finally placing it in an ideal position with respect to the tissues 61, 62 to be stapled.

Figure 10:
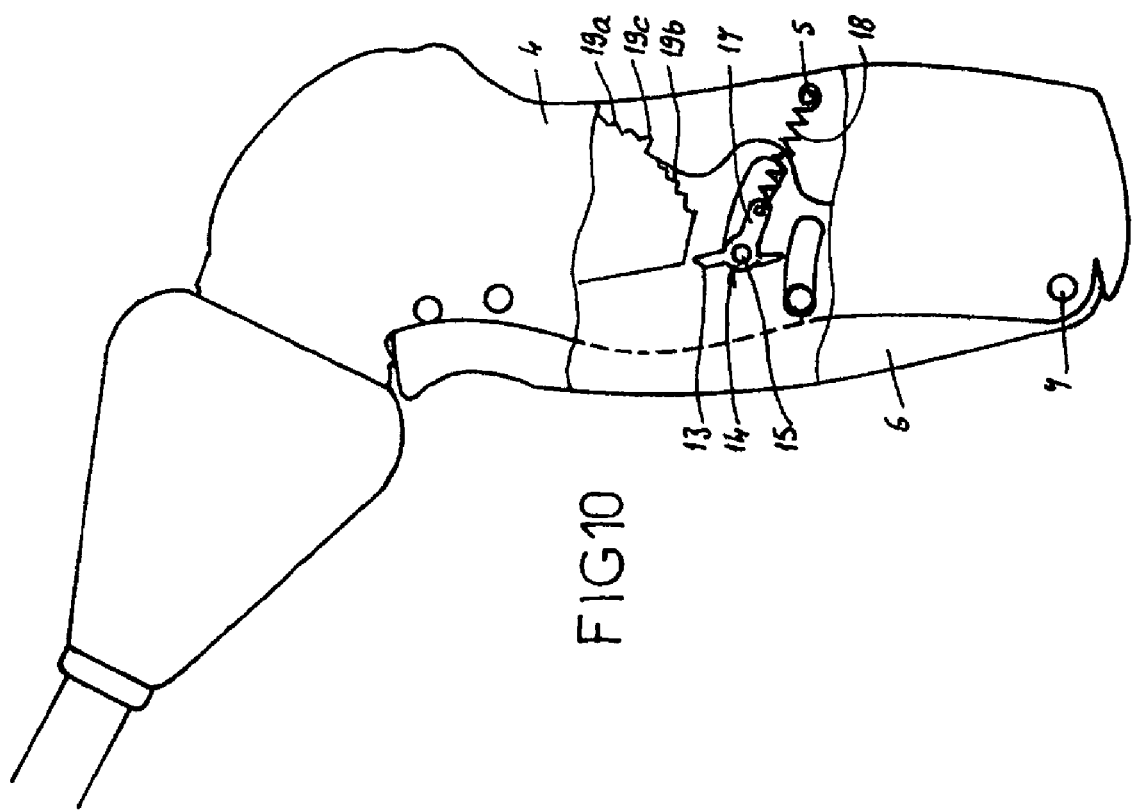

Once the surgeon has pressed sufficiently on the handgrip 6 for the branch 13 of the knurled wheel 14 to pass the tooth 19c, return is no longer possible, as shown in FIG. 9. In this figure, the branch 13 of the knurled wheel 14 is blocked against the tooth of larger size 19c. During the second part of the travel, the surgeon must proceed with the ejection of the fastener. To avoid incorrect use of the appliance, which could lead to its becoming jammed, the surgeon's manoeuvre is guided until its completion. Thus, during this second part of its travel, the branch 13 of the knurled wheel 14 cooperates with the series of more strongly inclined teeth 19b to permit continuation of the manoeuvre, tooth by tooth, while preventing release of the handgrip and, consequently, a reverse movement. Thus, the surgeon is obliged to press on the handgrip until the end of its travel, as is shown in FIG. 10, in order to free the branch 13 from the teeth 19b and thus trigger the ejection of the fastener A.

During this second part of the travel, the second control lever 10 has caused displacement of the piston 25 and, consequently, of the tube 38 and the push rod 42, the displacement of the push rod 42 taking place relative to the magazine slide 22, which remains temporarily fixed.

The push rod 42 is thus displaced longitudinally so that its end comes into contact with the proximal end of the anchoring bar 2 of the fastener A arranged in the receiving seat 55 and it pushes this anchoring bar into the ejection barrel 50, as is shown in FIG. 14.

The movement of the anchoring bar 2 pulls the connecting strip 4 and the catching bar 3 of the fastener that is in the process of being distributed. The distal end 3a of the catching bar 3 comes into abutment against the finger 59, causing this bar to pivot upwards until it is standing up parallel to the reinforcement 61. During this movement, its proximal end 3b meets the sloping face 51a of the rib 51 which drives this end transversely so that, once the bar 3 has righted itself, this end does not abut against the ejection barrel 50, but on the contrary moves away from the latter.

During this movement, the anchoring bar 2 advances along the ejection barrel 50. When the connecting strip 4 escapes from the latter, the bar 2 can begin to tilt with the aid of the catching bar 3. What happens is that, via the connecting strip 4, the organized movement of the catching bar 3 has the effect of retaining the anchoring bar 2 which is thus forced to right itself and to anchor in the biological tissues 62 as shown in FIG. 15. Because of the unbevelled shape of the ejection barrel 50 and the small overall size of the anchoring bar 2, the latter escapes rapidly from the ejection barrel 50 and then only needs a little space to right itself and rotate, as shown in FIGS. 15 and 16. The appliance 1 according to the invention and its fastener thus make it possible to staple prostheses in the area of anatomical structures of small thickness.

Finally, during or at the end of the righting of the anchoring bar 2, the catching bar 3, which is more or less parallel to the textile reinforcement 61, slides, via its distal end 3a, over the sloping face 59a of the finger 59 which drives it transversely and releases it.

The length of the projecting part of the ejection barrel 50 at the moment of ejection may be 3 mm for example.

Figure 11:
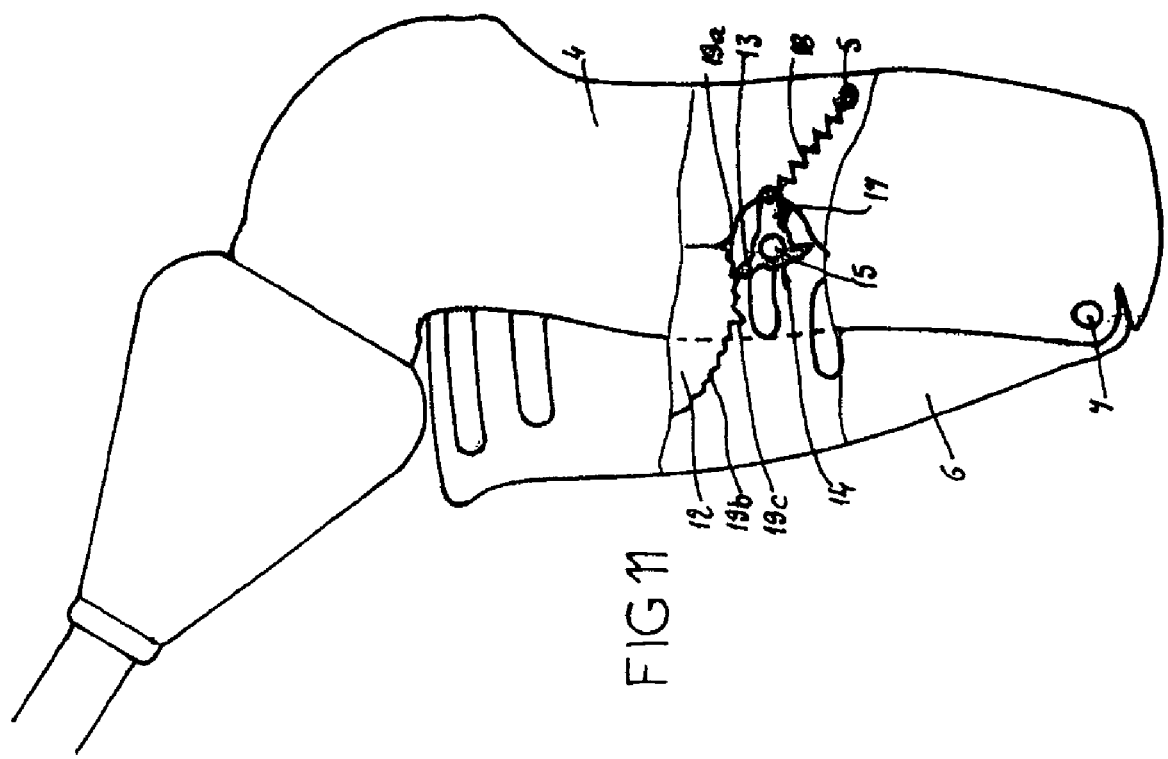

At the end of this movement, and as shown in FIG. 16, the release of the action on the handgrip 6 allows the spring 27 to return the magazine slide 22 and the push rod 42. During the release of the handgrip 6, the branch 13 of the knurled wheel 14 cooperates with the series of teeth 19a, 19b, 19c in order to prevent the user from again pressing on the handgrip before the latter has returned to its rest position, as shown in FIG. 11. This second non-return system once again prevents inappropriate use of the appliance and ensures that it does not become jammed. The arc of a circle 12 of the first control lever 8 and the series of teeth 19a, 19b and 19c form, with the branch 13 of the knurled wheel 14, a double non-return system ensuring that the appliance is used correctly and does not become jammed.

Once the handgrip 6 has returned to the rest position, the appliance 1 can be used for the subsequent fixations or can be withdrawn from the human body, as shown in FIG. 17.

While the fastener A is being distributed, the distribution means employed allow the anchoring bar 2 and the catching bar 3 to right themselves in order to ensure perfect retention of these tissues.

During the phase of distribution of the first fastener A, as shown in FIGS. 14 to 16, the receiving seat 55 is closed off by the push rod 42 and the awaiting fasteners maintain their position by virtue of a brake block (not shown) which is integral with the magazine slide 22. The movement of the magazine slide 22 towards the front of the appliance carries with it the stock of fasteners and therefore moves them away from the free end of the abutment rod 41, which is not set in motion until the end of the movement of the push rod 42.

As shown in FIGS. 5 to 7, the movement of the abutment rod 41 is brought about by the advance of the shuttle 32 on the rack 28.

Before use of the appliance 1, as shown in FIGS. 4 and 5, the shuttle 32 is locked at one and the same time in a recess 35 of the tubular body 20 via the projection 37 of its proximal tab 36 and also in a notch 29 of the rack 28 via its distal tab 33. At the moment when the fastener is ejected, the piston 25, pushed by the first control lever 8, advances in the distal direction, carrying with it the tube 38 and the flange 39 of this tube. As is shown in FIG. 6, the flange 39 comes into contact with the proximal block 31 of the rack 28 and moves this rack 28 in the distal direction. During this movement, the shuttle 32 is held integral with the rack via its distal tab 33 locked in the notch 29 of the rack, while its proximal tab 36 deflects so as to allow the projection 37 to pass the recess 35 of the tubular body 20, in which it was locked, and to lock in the following recess 35. Thus, the shuttle 32 and the abutment rod 41 integral with the latter advance in the distal direction by the length of a step P.

After the fastener has been ejected, the magazine slide 22 is returned by the spring 27 and its proximal end comes into contact with the distal block 30 of the rack 28. As is shown in FIG. 7, the magazine slide 22 thus drives the rack 28 along with it in the proximal direction. On account of the sloping face 34 of the distal tab 33 of the shuttle 32, the rack 28 moves in the proximal direction relative to the shuttle 32, which for its part remains stationary in relation to the tubular body 20 because of its projection 37 locked in the second recess 35 of this tubular body 20.

Thus, in FIG. 7, the shuttle 32 has advanced on the rack 28 by a step P in the distal direction compared to FIG. 5. This has the effect that the abutment rod 41, which is integral with the shuttle 32, has also advanced by a step P compared to the initial position that it occupied. In this way, upon the return of the magazine slide 22, the catching bar 3 of the last fastener comes into contact with the distal end of the abutment rod 41 and retains the row of fasteners, while the magazine slide completes its return in the tubular body 20.

At the end of the return of the magazine slide, the anchoring bar 2 of the first fastener comes into contact with the ramp 54, shown in FIG. 19, which ramp ensures its transfer into the receiving seat 55.

The appliance which has been described, and its fastener, are especially suitable for stapling prostheses such as parietal reinforcements without causing trauma to the flesh and without risks of haemorrhage. They are also especially useful for stapling prostheses in the area of anatomical structures of small thickness, for example Cooper's ligament, while ensuring very effective fixation, preferably only for the period of time required for fixation, on account of the preferably bioabsorbable nature of the fasteners. Moreover, the appliance and the fastener according to the invention can be used with the same effectiveness in surgical interventions performed by laparoscopy or, by contrast, open surgery.

The invention claimed is:

1. An assembly comprising at least one couched I-shaped surgical fastener (A) and an appliance (1) for storing, distributing and placing such fasteners, comprising:
   a handgrip body (B) equipped with at least one control means (8, 10) and an elongate element (C) attached and fixed to the handgrip (4), in which appliance the elongate element (C) is made up of a body (20) of tubular overall shape containing:
      a magazine slide (22) movable through the elongate element (C) and being configured and dimensioned to retain the at least one surgical fastener (A), each surgical fastener (A) including an anchoring bar (2), a catching bar (3) and a connecting strip (4), said magazine slide (22) being movable through the elongate element (C) by a control rod (24) which can be actuated by the control means (8, 10) of the handgrip (6), the magazine slide (22) being secured to a slotted and longitudinal hollow ejection barrel (50) projecting from the distal end of said magazine slide (22) and able to project from the elongate element (C), and,
      the tubular body (20) including means (23, 41) for distributing the stored fasteners (A) one by one via transfer of the anchoring bar (2) into a receiving seat (55) formed in the magazine slide (22), wherein an ejection plunger (42) is operatively connected to the control means (8, 10) of the handgrip (6) and positioned in alignment with the ejection barrel (50) so as to push the anchoring bar (2) of the fastener into the ejection barrel, characterized in that:
         the anchoring bar includes a cylindrical portion and a conical portion extending distally from a distal end of the cylindrical portion, the conical portion including a distal tip having a hemispherical shape,
         the surface of the distal end of the ejection barrel (50) is arranged in a plane substantially perpendicular to the longitudinal axis of the tubular body (20).

2. An assembly including an appliance (1) and a plurality of I-shaped surgical fasteners (A), comprising:
   a handgrip body equipped with at least one control means (8, 10), and
   an elongate element (C) attached and fixed to the handgrip (4), in which appliance the elongate element (C) is made up of a body (20) of tubular overall shape containing:
      near its distal end, a magazine slide (22) itself containing couched I-shaped fasteners (A), each fastener (A) having an anchoring bar (2), a catching bar (3) and a connecting strip (4), said magazine slide (22) being displaceable in the elongate element (C) by a control rod (24) which can be actuated by the control means (8, 10) of the handgrip (6), the magazine slide (22) being secured to a slotted and longitudinal hollow ejection barrel (50) projecting from the distal end of said magazine slide (22) and able to project from the elongate element (C), and
      means (23, 41) positioned within the tubular body (20) for distributing the stored fasteners (A) one by one, this distribution involving the transfer of the anchoring bar (2) of the first fastener into a receiving seat (55) formed in the magazine slide (22) and, an ejection plunger (42) which can be displaced by the control means (8, 10) of the handgrip (6) and which is arranged in alignment with the ejection barrel (50) so as to push the anchoring bar (2) of the first fastener in the ejection barrel, characterized in that:

the anchoring bar includes a cylindrical portion and a conical portion extending distally from a distal end of the cylindrical portion, the conical portion including a distal tip having a hemispherical shape; and the surface of the distal end of the ejection barrel (50) is arranged in a plane substantially perpendicular to the longitudinal axis of the tubular body (20).

3. Appliance (1) according to claim 2, characterized in that the ejection barrel (50) is made of plastic and is moulded in one piece with the magazine slide (22).

4. Appliance according to claim 2, characterized in that the fastener (A) is made of biocompatible plastic.

5. Appliance according to claim 4, characterized in that the fastener (A) is made of bioabsorbable plastic.

6. Appliance (1) according to claim 5, characterized in that the bioabsorbable plastic is a lactic acid polymer.

7. Appliance (1) according to claim 2, characterized in that the length of the projecting part of the ejection barrel (50) at the moment of ejection is less than or equal to 3 mm.

8. Appliance (1) according to claim 2, characterized in that the total length L' of the fastener (A) in its operating position is less than or equal to 10.5 mm.

9. Appliance (1) according to claim 2, characterized in that the total height H of the fastener (A) in its operating position is less than or equal to 6.1 mm.

10. Appliance (1) according to claim 2, characterized in that the elongate element C comprises a step-by-step system (23) able to move the stored fasteners A by a step P having a value equal to the length L of the catching bar (3) of a fastener A, this step-by-step system (23) comprising a rack (28) effecting a drawer movement upon each ejection and being equipped with a shuttle (32) which is mounted so as to slide on this rack (28), this shuttle (32) cooperating with fixed notches (35) of the magazine slide (22) in order to advance by a step P on the rack (28) upon each ejection.

11. The appliance according to claim 2, further comprising a projecting tooth extending radially from the conical portion of the anchoring bar.

12. The appliance according to claim 2, further including a non-return mechanism adapted for allowing repeated repositioning of the handgrip between a first position and a second position without repositioning the control rod, the non-return mechanism including a control lever operably coupled to a wheel, wherein a tooth of the control level engages a branch of the wheel as the handgrip is repositioned from the second position toward a third position, thereby inhibiting the handgrip from returning to the first position until completion of an actuation stroke.

* * * * *